United States Patent [19]

MacPhee et al.

[11] 4,362,179

[45] Dec. 7, 1982

[54] METHOD AND APPARATUS FOR CONTROLLING INK VISCOSITY

[75] Inventors: John MacPhee, Rowayton; William W. Barton, Stamford, both of Conn.

[73] Assignee: Baldwin-Gegenheimer Corporation, Stamford, Conn.

[21] Appl. No.: 191,290

[22] Filed: Sep. 26, 1980

[51] Int. Cl.³ ............................................ G05D 11/00
[52] U.S. Cl. .......................................... 137/3; 137/91; 137/92; 101/364; 101/DIG. 24
[58] Field of Search ................. 137/3, 91, 92; 73/448; 101/170, 349, 350, 364, 365, DIG. 24, 202, 363

[56] References Cited

U.S. PATENT DOCUMENTS

| | | | |
|---|---|---|---|
| 31,100 | 1/1861 | Adams | 73/448 |
| 174,240 | 2/1876 | Hicks | 73/448 |
| 2,707,916 | 5/1955 | Smith et al. | 101/363 |
| 2,969,016 | 1/1961 | Crosfield et al. | 101/202 |
| 3,485,257 | 12/1969 | Gegenheimer et al. | 137/91 |
| 3,557,817 | 1/1971 | Royse | 137/91 |
| 3,605,782 | 9/1971 | Hollis et al. | 137/91 |
| 3,667,500 | 6/1972 | Stone | 101/364 |
| 3,712,117 | 1/1973 | Fitzgerald et al. | 137/92 |
| 3,869,984 | 3/1975 | Toth | 101/349 |
| 3,901,149 | 8/1975 | Schulte-Kulkmann | 101/349 |
| 4,130,126 | 12/1978 | Chocholaty et al. | 137/91 |

Primary Examiner—H. Jay Spiegel

[57] ABSTRACT

A system for controlling the viscosity of flexographic and gravure printing ink. The system includes a variable weight hydrometer which monitors the density of circulating printing ink. The hydrometer is in cooperative relationship with a supply of solvent. When the density goes above a predetermined level solvent is fed to the ink until the predetermined level is reached.

4 Claims, 9 Drawing Figures

METHOD AND APPARATUS FOR CONTROLLING INK VISCOSITY

BACKGROUND OF INVENTION

This invention relates to controlling the viscosity of printing ink and is particularly useful in connection with flexographic and gravure printing presses.

In printing presses adapted to use the flexographic process inking systems are used having relatively few rollers for transferring the ink from the ink fountain roller to the plate cylinder which transfers the ink to a running web or the like.

Printing presses designed to utilize the flexographic process are characterized by the use of a resilient relief plate, relatively fluid inks, and inking systems which comprise relatively few rollers. In such systems the ink is generally metered by means of flooded nip. It has been found that, in such metering systems, the only fliud property which affects the thickness of the metered ink film is viscosity. In other words the more viscous the ink is, the thicker the ink film. Of course, when thicker ink films are applied less web length can be printed with a given volume of ink, assuming that speed, roller hardness and roller pressure are all maintained constant, and consequently there is a loss of ink mileage. The importance of viscosity has a very practical significance since flexographic inks contain relatively large amounts of volatile solvents. During the course of a press run, these solvents can and do evaporate rapidly causing an increase in ink viscosity and a corresponding decrease in ink mileage. Thus, one of the problems faced by flexographic press operators, in maintaining uniform print density and ink mileage, is to periodically monitor ink viscosity and to add solvent as necessary to maintain or control viscosity at a constant value.

Historically, controlling ink viscosity was done by the pressman using a Zahn Cup (i.e., Zahn Viscosimeter manufactured by Instrument Department, General Electric Company, West Lynn, Mass.) or similar manual viscometer. A Zahn Cup is a bullet-shaped 44 cc cup with a precision drilled orifice in its bottom. Viscosity is measured by dipping the cup into the liquid being tested, withdrawing it, and then measuring the time (usually in seconds) required for the full volume (44 cc) of liquid to flow out the orifice. Viscosity thus measured is expressed as the time in seconds for the fluid to drain out and the number of the Zahn Cup. Although typically, a flexographic ink may have a viscosity of 20 seconds, Zahn Cup #2 (about 30 centipoise or the consistency of milk) the viscosities of flexographic inks in use today vary over a wide range, depending on the type of substrate being printed. The relationship between Zahn Cup No. 2 in seconds verses centipoise is illustrated in Chart I.

After determining viscosity, the pressman then manually adds and mixes in solvent with the ink, as necessary, to maintain a constant value of viscosity.

The success of the manual control procedure of adjusting viscosity depends on the skill of the pressman; how often he takes samples and on his ability to judge how much solvent should be added when an increase in viscosity has been observed.

Another problem with flexographic inks is that pigment density in the ink will increase as solvent is lost, with the result that an excess amount of pigment will be used even if film thickness remains constant. Thus, ink mileage also will be adversely affected in those types of flexographic presses in which the metered ink film thickness is not viscosity dependent such as those which use a reverse angle doctor blade and an engraved roller to meter the ink film thickness. This situation also occurs in gravure presses, where the doctor blade wipes the ink from the surface of the printing cylinder leaving ink only in the cells or cavities below the surface of the cylinder.

In short, it is necessary to control the viscosity of flexographic ink during a press run in order to maintain print density and economize on ink usage. There are, however, several additional problems associated with controlling ink viscosity.

First, the system must control viscosity over a relatively wide range - approximately 20–200 centipoise, which corresponds to thin milk on the low end and SAE 20 motor oil at 60° F. on the high end.

Second, the viscosity must be controlled to within ±10% of control point in poise e.g., better than ±0.5 seconds for a control point of 20 seconds, Zahn Cup #2 and must be designed in such a way that clogging of passages and openings by ink is prevented.

In addition, the device must be easy to clean, have a rugged construction so as to stand up under pressman abuse, be simple to set up for inks of different viscosities and be low in cost.

There are in the prior art numerous devices which have been used to automatically control the viscosity of flexographic and gravure inks. The operating principles of the various types are described below:

One type of prior art device can be referred to as the efflux cup type. This device is an all mechanical controller in which the trajectory of a stream of ink flowing from an orifice under constant head varies with the viscosity. As the viscosity increases, the trajectory shortens, causing the ink to have to flow into an ink cup having a drain hole. When the rate of flow into the cup becomes greater than the drain capability, the cup fills. As the weight in the ink cup increases, the cup drops downward causing the solvent cup to rise, tripping the solvent valve lever, which opens the solvent valve. The flow rate into the solvent cup is greater than its drain capability and the cup fills. In time, the weight of the solvent cup offsets the weight of the ink cup, and the solvent cup drops, automatically shutting off the solvent supply. The ink cup returns to its original up position. The solvent drains from the solvent cup into the ink stream. This general type of device is described and shown in U.S. Pat. No. 2,597,472.

Another type of viscosity control device is the falling piston type. There are several forms of this device. In one form of this device viscosity is measured as a function of the time required for a weighted piston to sink into a sample-filled chamber against the resistance of the fluid as the movement forces the fluid through the annular clearance between the piston and chamber wall. The time for each cycle is a measure of viscosity. The piston is periodically raised by an air-operated mechanism.

The measure of viscosity is electrically transmitted to the controller, where it may be indicated or recorded. When the viscosity exceeds the control point setting, a solvent solenoid valve opens, thereby adding solvent to the ink. The solvent valve contains an adjustable port, which is set to correct the viscosity error without excessive overshooting. The falling piston type is sold by Norcross Corp., Newtown, Mass.

Another type of viscosity control device is based on the time required for longitudinal vibrations of a rod immersed in the ink to subside. A solid-state electronic sub-assembly produces a short pulse of current to a coil situated inside the probe. Once the pulse sets the magnetostrictive blade of the probe in longitudinal motion, no other pulse is generated until the vibration amplitude is dampened to a predetermined level. The "viscosity" of the ink determines when a drive pulse will be generated, thereby providing the base for measurement. That is, the higher the "viscosity" of the ink, the greater the dampening exerted on the vibrating blade, resulting in a more frequent drive pulse being generated. This measurement is reported to the indicator and/or recorder and to the solvent solenoid valve controller in terms of the product of the ink's viscosity and specific gravity. Because viscosity and specific gravity are both inverse functions of temperature, a temperature probe and automatice compensation circuitry are usually employed in conjunction with the viscosity controller. This type of device is sold by the Environmental & Process Instruments Division, Bendix Corp., Lewisburg, W. Virginia under the trade name Ultra-Viscoson Viscometer Model 1800.

A flexural viscosity controller includes a detector consisting of a U-shaped spring rod immersed in the ink stream. One end is excited at 120 hertz by a pulsating magnetic field. The amplitude of the vibration depends on the viscosity of the ink. When the viscosity increases, the resistance to the shearing action of the probe increases and the amplitude of vibration decreases. At the detector, the vibration of the pick-up armature in the field of a permanent magnet induces a 120 hertz voltage in the coil which is proportional to the amplitude of vibration of the probe and thus to the viscosity of the ink. This output signal is converted to a millivolt DC signal to be compatible with standard recorders and controllers. Such a device is sold by Automation Products, Inc., Houston, Texas, under the trade name Dynatrol.

A torsional type of viscosity control device includes variable gain amplifier which drives a magnetic coil that causes a spherical torsional member to oscillate at its natural frequency in the ink pipeline or reservoir. The amplitude of the oscillations is sensed as an AC voltage by an amplitude-monitoring circuit. The voltage is rectified and referenced to a DC voltage equivalent to that obtained when the sphere oscillates in air. The resulting error signal is used to control the gain of the amplifier in order to maintain the amplitude of mechanical oscillation at the reference level over a wide range of viscous loss. The viscosity is obtained from the power required for the magnetic coil to maintain the constant amplitude. U.S. Pat. Nos. 3,382,706; 3,762,429, 3,712,117; and 3,710,614 relate to such torsional type devices.

In another torque type device the viscosity is measured by sensing the viscous drag imposed on a disc or cylinder rotated in the ink at constant speed through a torsion element. An increase in viscosity will cause a beryllium copper spring in the torsion element to wind up, while a decrease will allow the spring to unwind. The drive is either an air motor or an electric synchronous motor. A pickup converts the torque of the element to a pneumatic signal which is transmitted to a controller and an indicator or recorder. The pneumatic controller opens a solvent valve if the sensed viscosity is greater than the preset valve. Solvent will then be added until the set point is attained at which time the controller closes the valve. The measuring range can be changed by unhooking one spindly from the drive extension and hooking on another spindle. No recalibration is required. Such a device is manufactured by Brookfield Engineering Laboratories, Inc., and sold by Viscosel Corp., Stoughton, Massachusetts.

Another prior art type device includes an electronic unit which measures viscosity in conjunction with a sensing motor fitted with a disc immersed in the ink. The current drawn by the sensing motor is proportional to the motor's torque and hence represents the viscosity of the ink. The current is compared with a preset value by the electronic control unit, and the measured deviation initiates the opening of a solenoid valve, thus causing the addition of the required amount of solvent. This type unit is sold by Controle & Automation Div., Chambon, Orleans-la Source, France, under the trade name D.A.S. 2000.

In another prior art device when the drag of the ink on a rotating cylindrical body decreases the number of revolutions under a preset value, a signal is transmitted to a transistorized regulation unit which opens the electromagnetic valve in the solvent line until the preset revolutions is again attained. The above device is sold by Anderson & Vreeland East, Inc., Fairfield, New Jersey.

In a flow matching type device, the ink enters a measuring cell through a calibrated hole and is discharged through a special nozzle. The flow resistance of the outlet nozzle is greater than that of the inlet hole. This condition causes the level of the ink in the measuring cell to rise until the level is sensed by pneumatic detector which opens a valve to admit solvent. When the preset viscosity is attained solvent feed stops. The desired viscosity is set by adjusting the pneumatic detector elevation by means of a threaded rod. A push button is provided for manual solvent addition. There is also an "optical addition indicator". The above device is sold by Selectra S.P.A., 22059 Robbiate (Co.) via Piave 11, Italy.

The prior art devices, described above, all utilize an ink monitoring principle which is based on a physical phenomena that is dependent or varies with ink viscosity. Examples of such phenomena are the drag exerted on a falling or rotating body in the ink, the trajectory of a stream of ink, and the dampening effect exerted by the ink on a vibrating member immersed in it. Although these techniques are sound in theory, their implementation involves either the use of small passages which can easily become clogged with ink or the use of delicate mechanisms which can easily be damaged.

Viscosity and density are different properties in that viscosity is a measurement of resistance to flow whereas density is a measurement of weight per unit volumes i.e. specific gravity. For liquids of different chemical compositions there is no correlation between viscosity and density. Thus, for example, water has a higher density than oil but has a much lower viscosity.

In Chart II there is charted the specific gravity and the viscosity of eleven (11) liquids of different chemical composition ranging from carbon tetrachloride to water. As Chart II illustrates there is no correlation between density and viscosity for the liquids plotted.

Generally speaking, printing ink consists of pigment, resin and solvent wherein the solvent is less dense or lighter than the other constituents. Moreover, solvent being volatile evaporates so that after a period of time the ink becomes more dense.

It has been found, that for any given printing ink used in flexographic and gravure printing there is a correlation between viscosity and density. This fact is illustrated by Charts III and IV.

In Chart III there is charted viscosity (Zahn Cup No. 2) and specific gravity versus the pounds of solvent per one hundred (100) pounds of a given ink. The solid line illustrates that as solvent is added the viscosity decreases; whereas the dotted line illustrates that as solvent is added the density decreases. While these charts specifically relate to white polyamide ink for use on plastic film, it has been found that the same phenomena occurs with respect to other flexographic and gravure inks.

Thus, it has been found that as a solvent such as ethyl alcohol is added to a given printing ink there is a definite relationship between density and viscosity as can be seen in Chart IV which plots density and viscosity of an ink to which ethyl alcohol is added. Thus although there is no correlation between density and viscosity for fluids of different chemical compositions, there is a correlation for a fluid of given composition when that composition is varied by changing the concentration of one of the constituents.

It has been determined through measurements that a ten (10) percent variation in ink viscosity (when measured in centipoise) can be detected by measuring the corresponding variation in ink density. In addition, it has been found that hydrometer structures can regulate ink viscosities and that a hydrometer can be adjusted so as to regulate a wide variety of ink viscosities. The polyamide ink, for example, is used at viscosities as low as 17 seconds, Zahn Cup #2, and a viscosity control of $\pm\frac{1}{2}$ second was necessary for proper control. For this case, the variation in specific gravity, corresponding to a $\frac{1}{2}$ second variation in viscosity, is found from Chart IV to be 0.012. Thus, the desired accuracy of the specific gravity controller is $\pm 0.012$, which is well within the accuracy of the hydrometer control valve. It has been found that the accuracy of the hydrometer control valve is $\pm 0.0012$ when controlling isopropyl alcohol concentrations in fountain solution.

OBJECTS OF THE INVENTION

With the foregoing in mind it is an object of this invention to provide a new and improved system for controlling the viscosity of printing ink.

Another object of this invention is to provide a method of controlling and maintaining the viscosity of printing ink at a predetermined level.

A further object of this invention is to provide an apparatus for controlling and maintaining the viscosity of printing ink at a predetermined level.

A further object of this invention is to provide a system for controlling the viscosity of printing ink by monitoring the density of the printing ink which is particularly useful with flexographic and gravure inks.

A further object of this invention is to provide a hydrometer-like device which moves in response to the density of the printing ink to control the viscosity of the ink.

A still further object of this invention is to provide a device which is adapted to control the viscosity over a relatively wide range of viscosities by the addition of solvent when the density goes above a predetermined level.

Another object of this invention is to provide a system, apparatus and method for monitoring the density of printing ink with a hydrometer-like device which causes the addition to solvent to the printing ink when the density goes above a predetermined level and feeds solvent until the density reaches a predetermined level.

Additional objects and advantages of the invention will be set forth in the description which follows and, in part, will be obvious from the description; the objects and advantages being realized and obtained by means of the instrumentation, parts, apparatus, system, steps and procedures particularly pointed out in the appended claims.

BRIEF DESCRIPTION OF THE INVENTION

Briefly described, the present invention is founded on the concept of controlling printing ink viscosity by monitoring its density and adding a less dense ingredient, i.e. solvent, to the printing ink when the density reaches a predetermined level.

The invention involves controlling the ink viscosity by constantly and automatically monitoring the density of the ink and adding solvent automatically when the density of the printing ink falls below a predetermined level until such time that the density reaches the predetermined level at which time the solvent feed is stopped.

The invention utilizes a hydrometer controlled valve somewhat similar to that shown described in U.S. Pat. No. 3,485,257. In the present instance the hydrometer and its associated valve automatically monitors ink density and automatically supplies solvent when the density reaches a predetermined level so as to maintain a constant ink density and thus a constant ink viscosity.

The invention consists of the novel parts, construction, arrangements and improvements shown and described.

The accompanying drawings which are incorporated in and constitute a part of this specification illustrate an embodiment of the invention and together with the description serve to explain the principles of the invention.

DETAILED DESCRIPTION OF THE INVENTION

Figure 1:
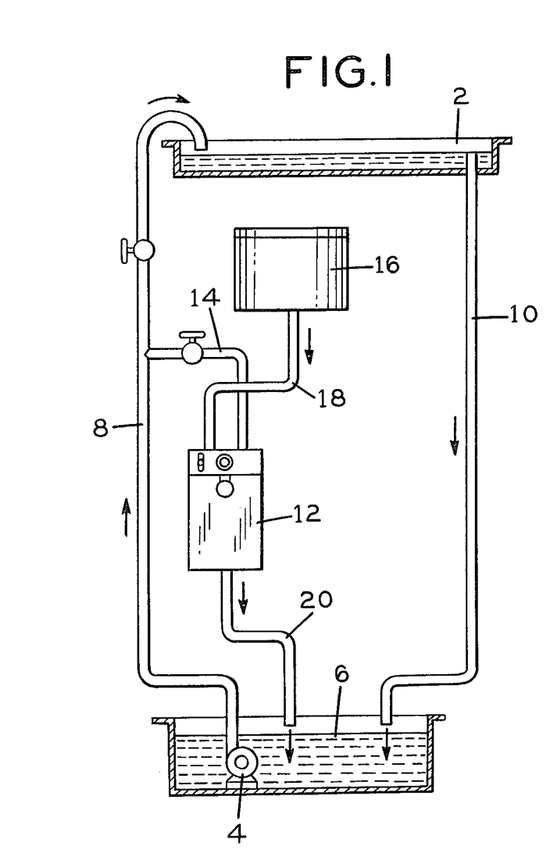
FIG. 1 is a schematic view of the recirculating ink system and the control mechanism for monitoring ink density.

Referring to FIG. 1 there is shown a schematic view of a recirculating system in accordance with the present invention. As shown, there is an ink fountain or pan 2 adapted to be positioned adjacent a conventional ink metering roll system (not shown) of a flexographic printing press.

The ink fountain or pan 2 is supplied through passage 8 with printing ink by a pump 4 which is in the ink supply 6. The ink is returned from the ink fountain pan 2 to the printing ink supply 6 through line 10.

A primary purpose of this invention is to provide a system for controlling the viscosity of the printing ink. More particularly, in accordance with this invention means is provided for controlling the viscosity of the ink by monitoring and controlling the density thereof.

This means includes a control mechanism 12 positioned so that at least a portion of the printing ink is directed by by-pass line 14 to control mechanism 12.

There is a supply of solvent 16, which has a lower density than the printing, adapted to be directed to the control mechanism by a line 18. The control mechanism maintains the density of the printing ink at a predetermined level and the ink is then returned to the ink supply 6 through line 20.

Alternatively, the control means 12 may be located in the return line 10 or supplied by a separate pump directly from the ink supply 6 as shown in U.S. Pat. No. 3,485,257 which relates to a fountain solution system.

Figure 2:
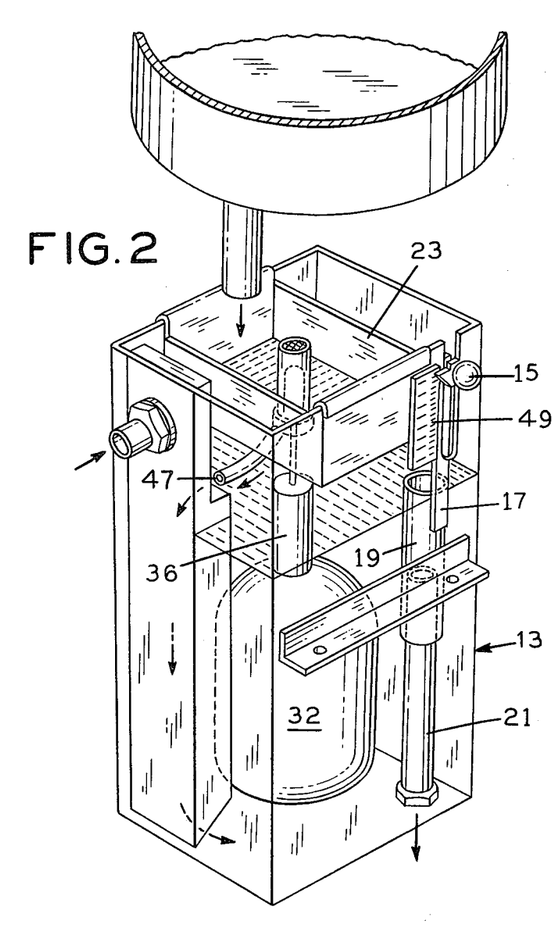
FIG. 2 is a perspective view partially broken away of the control mechanism of the invention.

The control mechanism includes a removable sub-reservoir or tray 23 positioned adjacent the top of the control tank 13 which is feed solvent from reservoir 16. The level of liquid in the tank 13 is determined by the adjustment knob 15 which is connected by member 17 to the sliding tube 19 which is in telescoping relationship with discharge pipe 21.

It will be understood that for a given hydrometer float the level of liquid in the tank 13 will determine the density.

When the level of liquid in the tank is low, the density is high and when the level of liquid is high the density is low. This occurs because the float weight equals the volume of displaced liquid times its density. Thus, by moving the knob upwardly or downwardly the level of liquid in the tank can be varied and the density varied within limits for a given float.

Figure 3:
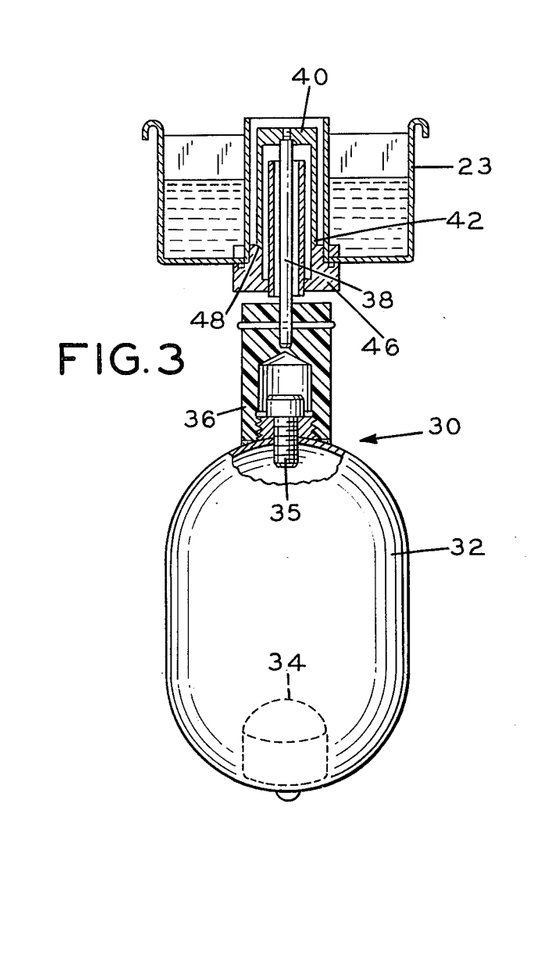
FIG. 3 is a view partially in section of the one modification of the hydrometer and valve of the present invention.

Referring to FIGS. 2-3, there is shown the mechanism for monitoring the density of the printing ink.

As embodied, this means includes a hydrometer float 30 consisting of a hollow stainless steel bulb 32 which has a ballast weight 34 located at its bottom on the inside thereof. By changing the weight of the bolt 35 the weight of the float can be adjusted over a narrow range. Attached to the top of the bulb is a cylindrical stem 36 of lightweight material, such as polyvinylchloride. Attached to and extending above the stem is a slender stainless steel rod 38. This rod is attached by any convenient means at its upper end to an inverted stainless steel cup 40 which is shaped as a cartridge case. The lower end of the cup 40 is spherically contoured plug 42 and constitutes the plug half of the valve. Attached to the bottom of the sub-reservoir 23 is a valve body 46 having a spherically contoured valve seat 48 adapted to mate with the valve plug 42.

Referring to FIGS. 2 and 3, it can be seen that as the hydrometer bulb 32 rises and falls with density changes, the valve plug 42 will rise and fall and the valve will open and close, thus permitting or preventing the flow of solvent into the printing ink. When the valve is open solvent flows into tank 13 through tube 47.

As the density of the printing ink increases the hydrometer 30 rises thus opening the valve and permitting solvent to flow into the container thereby reducing the density of the printing ink to a predetermined level. When the density reaches a predetermined level the hydrometer falls thus closing the valve and preventing additional solvent flow.

It has been found that the printing ink can be kept within a range of preselected densities by varying the height of the liquid in the chamber in which the hydrometer is located. The desired preselected density range can be achieved by preselecting or specifying two parameters; the diameter of the cylindrical stem and the total weight of the hydrometer. The total weight of the hydrometer is changed by changing the ballast weight 34 or the bolt 35.

The following shows the density range for three hydrometers with stem diameter and float weight:

| No. | Stem Dia. (in.) | Float Wt. (gms.) | Density Range (specific gravity) |
| --- | --- | --- | --- |
| 1 | 2.40 | 1316 | 1.184–1.37 |
| 2 | 2.40 | 1158 | 1.04–1.20 |
| 3 | 1.06 | 965 | 0.965–1.000 |

The following are examples of several of the floats in actual use:

Float No. 1: This float was used to control the viscosity of a water based ink with a solvent consisting of fifty (50) percent water and fifty (50) percent ethyl alcohol. The ink was maintained at the desired viscosity of twenty-three (23) seconds Zahn Cup No. 2. The specific gravity was 1.34.

Float No. 2: This float was used to control the viscosity of an alcohol-base ink with a glycol ether solvent. The ink was maintained at the desired viscosity of twenty-three seconds Zahn Cup No. 2 (a specific gravity of approximately 1.15).

Float No. 3: This float was used to control the viscosity of an alcohol-base ink with ethyl alcohol and glycol ether solvent. The ink was maintained at a viscosity of twenty-seven (27) seconds Zahn Cup No. 2 which corresponded to a specific gravity of 0.970.

The initial positioning of the liquid in the reservoir 13 is as follows:

The pressman mixes an initial batch of ink to obtain the desired running viscosity by using a Zahn Cup or the like.

The knob 15 is set at the bottom of its range. This position of the knob maintains the level of the ink within the chamber is as its lowest elevation. Thus, the minimum volume of the float is immersed in the ink. Consequently, an ink denser than the density range of the float would be required to lift the float and open the solvent valve.

The pressman installs the reservoir 16 containing solvent to be added to the ink to control viscosity.

With ink of the desired viscosity (and density) for printing passing through the chamber, the control knob 15 is slowly raised until bubbles rising through the solvent reservoir indicated that the solvent is being fed into the ink. The knob is then lowered approximately 1/16 inch in order to prevent further dilution of the ink with solvent.

Figure 2A:
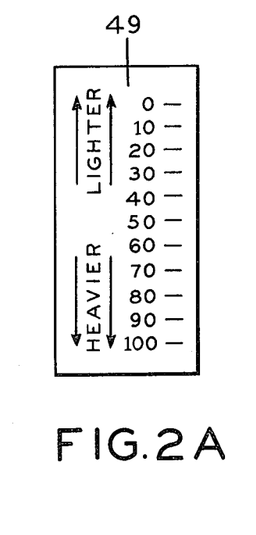
FIG. 2A is a view of the indicia scale.

As the solvent slowly evaporates from the circulating ink, solvent is automatically replenished by the invention, thereby maintaining a constant ink viscosity and density. If the press operator desired a lower viscosity ink, this is accomplished by moving the control knob up slightly. Similarly, a denser ink is obtained by lowering the knob. Notations on the scale 49, alongside the control knob indicate the directions to move the knob in order to obtain lighter or darker printing.

In this way the range of densities for each of the floats is determined by the position of the knob 15.

While the hydrometer float described above has proven satisfactory over a full range of densities for flexographic and gravure printng inks with which they have been used, it can be inconvenient to change from one float to another to accomodate different densities. Thus, since the ballast weight is located within the float bulb, it is not easily accessible if necessary to change the weight for another density range.

Figure 4:
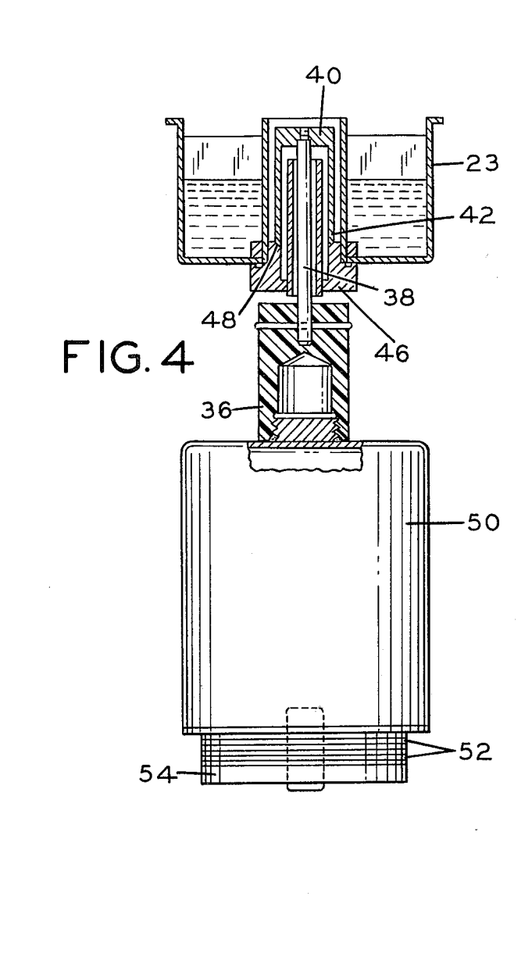
FIG. 4 is a view partially in section of the preferred embodiment of the hydrometer and valve of the present invention.

A preferred embodiment of a hydrometer structure useful in the present invention is shown in FIG. 4. In this embodiment there is a cylindrical float member 50 which permits an increase in the volume of the float member while permitting it to fit within the chamber.

In one preferred embodiment the weight of the float is about 1166 grams and the diameter of the stem is about 1½ inches. In accordance with this invention a plurality of disc shaped weighted wafers 52 are provided which are maintained in position by a retainer 54 which is removable attached to the bottom of the float member, by a threaded bolt or other similar means which passes through openings in the discs. The number of wafers and hence the weight of the float can be changed by adding or subtracting from the number of wafers.

With this float arrangement the density can be controlled over a range of 0.955 to 1.000 without a weight change. By adding up to ten wafers an overall density range of 0.955 to 1.405 can be accomodated. Each wafer weighs 58 grams.

We claim:

1. A method of maintaining the viscosity of printing ink at a predetermined level by monitoring the density of printing ink comprising:
    (a) circulating printing ink to and from a printing press and a source of supply;
    (b) monitoring the circulating printing ink in a control means which includes a tank adapted to receive the printing ink;
    (c) maintaining in said tank a hydrometer and associated stem, said hydrometer having a predetermined weight range and said stem having a predetermined diameter range necessary to give the predetermined viscosity range of the printing ink;
    (d) maintaining a supply of solvent in fluid communication with respect to said tank;
    (e) maintaining valve means in operative relationship with said hydrometer and stem and said supply of solvent; and
    (f) maintaining said hydrometer so that said hydrometer opens said valve means when the printing ink density goes above a predetermined level to allow solvent to enter said tank and said hydrometer closing said valve means when the density of the printing ink reaches the predetermined level to thereby maintain the viscosity of the printing ink at a predetermined level.

2. A method of maintaining the viscosity of printing ink within a predetermined range by monitoring the density of the printing ink comprising:
    (a) circulating printing ink to and from a printing press and a source of supply;
    (b) selecting a hydrometer having a predetermined weight and associated stem having a predetermined stem diameter so as to maintain the predetermined viscosity range for the printing ink;
    (c) monitoring the circulating printing ink in a control means which includes a tank adapted to receive the printing ink;
    (d) maintaining said hydrometer and stem in said tank so that the position of said hydrometer and stem changes with the density fo the printing ink;
    (e) maintaining a supply of solvent in fluid communication with respect to said tank; and
    (f) maintaining valve means in operative relationship with said hydrometer and stem and said supply of solvent; whereby said hydrometer opens said valve means when the printing ink density goes above a predetermined level so as to allow solvent to enter said tank until such time that said hydrometer and stem close said valve to thereby maintain the viscosity of the printing ink within the predetermined range.

3. A method of maintaining the viscosity of printing ink within a predetermined range by monitoring the density of the printing ink comprising:
    (a) circulating printing ink to and from a printing press and a source of supply;
    (b) monitoring the circulating printing ink;
    (c) selecting a hydrometer having a predetermined weight range and selecting a hydrometer stem having a predetermined diameter range, said selection being dependent on the desired predetermined viscosity range of the printing ink;
    (d) positioning said hydrometer and hydrometer stem in the circulating printing ink; and
    (e) using said hydrometer to monitor the density of the printing ink and maintaining the viscosity of the printing ink within a predetermined range by adjusting the density of the printing ink.

4. A system as defined in claim 3 including:
    (a) providing a plurality of weights so that the weight of the hydrometer can be selectively changed to obtain a predetermined viscosity range.

* * * * *